(12) United States Patent
San et al.

(10) Patent No.: US 9,487,804 B2
(45) Date of Patent: Nov. 8, 2016

(54) HYDROXY- AND DICARBOXYLIC-FAT SYNTHSIS BY MICROBES

(71) Applicant: William Marsh Rice University, Houston, TX (US)

(72) Inventors: Ka-Yiu San, Houston, TX (US); Xixian Xie, Houston, TX (US); Leepika Tuli, Houston, TX (US); Hui Wu, Houston, TX (US)

(73) Assignee: William Marsh Rice University, Houston, TX (US)

( * ) Notice: Subject to any disclaimer, the term of this patent is extended or adjusted under 35 U.S.C. 154(b) by 28 days.

(21) Appl. No.: 14/607,624

(22) Filed: Jan. 28, 2015

(65) Prior Publication Data

US 2015/0225753 A1 Aug. 13, 2015

Related U.S. Application Data

(60) Provisional application No. 61/939,567, filed on Feb. 13, 2014.

(51) Int. Cl.
| | |
|---|---|
| *C12N 9/16* | (2006.01) |
| *C12P 7/64* | (2006.01) |
| *C12N 15/52* | (2006.01) |
| *C12P 7/42* | (2006.01) |
| *C12P 7/44* | (2006.01) |

(52) U.S. Cl.
CPC ............... *C12P 7/6409* (2013.01); *C12N 9/16* (2013.01); *C12N 15/52* (2013.01); *C12P 7/42* (2013.01); *C12P 7/44* (2013.01); *C12Y 301/02014* (2013.01); *Y02P 20/52* (2015.11)

(58) Field of Classification Search
CPC ...... C12N 9/0008; C12N 9/16; C12P 7/6409
USPC ........................................................ 435/134
See application file for complete search history.

(56) References Cited

U.S. PATENT DOCUMENTS

| | | | |
|---|---|---|---|
| 7,223,567 B2 | 5/2007 | Ka-Yiu et al. | |
| 7,901,924 B2 | 3/2011 | San et al. | |
| 2013/0052700 A1 | 2/2013 | Poetter et al. | |
| 2014/0093921 A1 | 4/2014 | San et al. | |
| 2014/0193867 A1 | 7/2014 | San et al. | |
| 2014/0212935 A1 | 7/2014 | San et al. | |

FOREIGN PATENT DOCUMENTS

| | | |
|---|---|---|
| WO | WO2011116279 | 9/2011 |
| WO | WO2013024114 | 2/2013 |
| WO | WO2013096665 | 6/2013 |

OTHER PUBLICATIONS

Davis, M.S.; Cronan, J.E., Inhibition of *Escherichia coli* acetyl coenzyme A carboxylase by acyl-acyl carrier protein, Jr. J Bacteriol 183, 1499 (2001).

Golyshin P.N., et al., Oleiphilaceae fam. nov., to include *Oleiphilus messinensis* gen. nov., sp. nov., a novel marinebacterium that obligately utilizes hydrocarbons. Int J Syst Evol Microbiol 52:901-911 (2002).

Heath, R.J. & Rock, C.O. Inhibition of beta-ketoacyl-acyl carrier protein synthase III (FabH) by acyl-acyl carrier protein in *Escherichia coli*, J Biol Chem 271, 10996 (1996a).

Heath, R.J. & Rock, C.O., Regulation of fatty acid elongation and initiation by acyl-acyl carrier protein in *Escherichia coli*, J Biol Chem 271, 1833 (1996b).

Ishizuka M., et al., Overexpression of human acyl-CoA thioesterase upregulates peroxisome biogenesis, Exp Cell Res. Jul. 1, 2004;297(1):127-41.

Jing F., et al., Phylogenetic and experimental characterization of an acyl-ACP thioesterase family reveals significant diversity in enzymatic specificity and activity, BMC Biochemistry 12:44 (2011).

Julsing M.K., Outer membrane protein AlkL boosts biocatalytic oxyfunctionalization of hydrophobic substrates in *Escherichia coli*, Appl Environ Microbiol. 78(16):5724-33 (2012).

Lee S., et al., Heterologous co-expression of accA, fabD, and thioesterase genes for improving long-chain fatty acid production in *Pseudomonas aeruginosa* and *Escherichia coli*. Appl Biochem Biotechnol. May 2012;167(1):24-38.

Lee S1, Jeon E, Jung Y, Lee J. Liu C. & Shao Z., *Alcanivorax dieselolei* sp. nov., a novel alkane-degrading bacterium isolated from sea water and deep-sea sediment. Int J Syst Evol Microbiol 55(3):1181-1186 (2005).

Marchant R., et al., The degradation of n-hexadecane in soil by Thermophilic geobacilli. FEMS Microbiol Ecol 56 (1):44-54 (2006).

Meintanis C, et al., Biodegradation of crude oil by thermophilic bacteria isolated from a volcano island. Biodegradation 17:3-9 (2006).

Saerens S.M.G., et al., The *Saccharomyces cerevisiae* EHT1 and EEB1 genes encode novel enzymes with medium-chain fatty acid ethyl ester synthesis and hydrolysis capacity. J Biol Chem 281(7): 4446-4456 (2006).

Soyombo A., et al., Molecular Cloning and Expression of Palmitoyl-protein Thioesterase 2 (PPT2), a Homolog of Lysosomal Palmitoyl-protein Thioesterase with a Distinct Substrate Specificity, JBC 272(43): 27456-27463 (1997).

(Continued)

*Primary Examiner* — Tekchand Saidha
(74) *Attorney, Agent, or Firm* — Boulware & Valoir

(57) ABSTRACT

Systems, methods and microbes that allow the biological production of hydroxy fatty acids and dicarboxylic fatty acids are provided. Specifically, hydroxy fatty acids and dicarboxylic fatty acids are produced by microbes that have been engineered to overexpress acyl ACP thioesterase plus an alkane degration pathway, such as AlkBGT or AlkJH These can be in separate microbes or the same microbe, and separate microbes can be co-cultured or sequentially cultured. Continuously fed systems transferring secreted fats from one microbial culture to another can also be used.

16 Claims, 9 Drawing Sheets

(56) References Cited

OTHER PUBLICATIONS

Throne-Holst, M., Identification of Novel Genes Involved in Long-Chain n-Alkane Degradation by *Acinetobacter* sp. Strain DSM 17874, Appl Environ Microbiol. 73(10): 3327-3332 (2007).

van Beilen J.B., DNA sequence determination and functional characterization of the OCT-plasmid-encoded alkJKL genes of Pseudomonas oleovorans, Mol Microbiol. 6(21):3121-36 (1992).

Voelker T.A. & Davies H.M., Alteration of the specificity and regulation of fatty acid synthesis of *Escherichia coli* by expression of a plant medium-chain acyl-acyl carrier protein thioesterase, J. Bacteriol. 176:7320-7327 (1994).

Whyte, L.G. Gene Cloning and Characterization of Multiple Alkane Hydroxylase Systems in Rhodococcus Strains Q15 and NRRL B-16531, Appl. Environ. Microbiol.68(12): 5933-5942 (2002).

Yakimov M.M., et al., *Oleispira antarctica* gen. nov., sp. nov., a novel hydrocarbonoclastic marine bacterium isolated from Antarctic coastal sea water. Int J Syst Evol Microbiol 53:779-785 (2003).

Yakimov M.M., et al., *Thalassolituus oleivorans* gen. nov., sp nov., a novel marine bacterium that obligately utilizes hydro-carbons. Int J Syst Evol Microbiol 54:141-148 (2004).

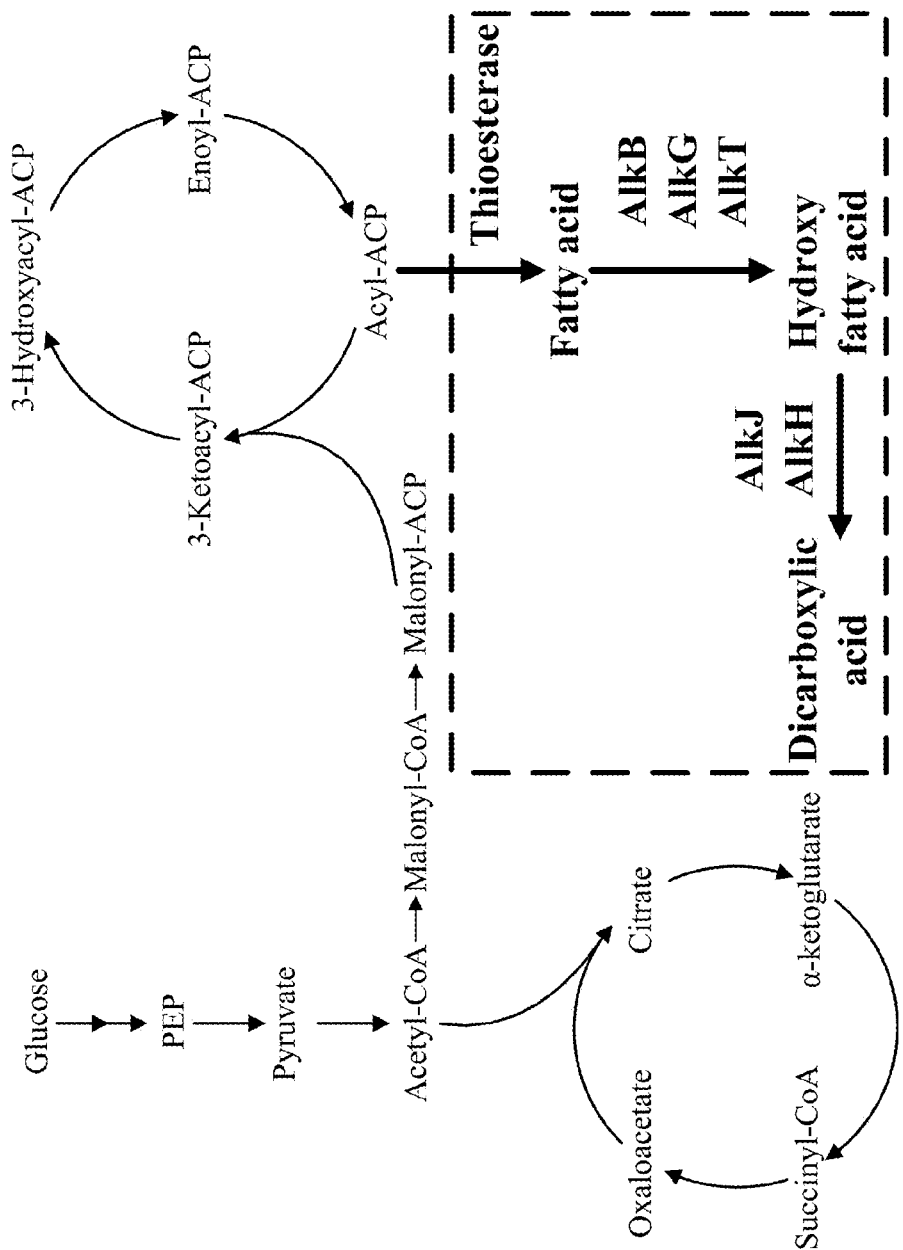
FIG. 1: Diagram showing the genetically engineered biosynthetic pathway of hydroxy fatty acid and dicarboxylic fatty acid. The bold arrows in the dotted box represent the newly introduced pathway of fatty acid derivatives.

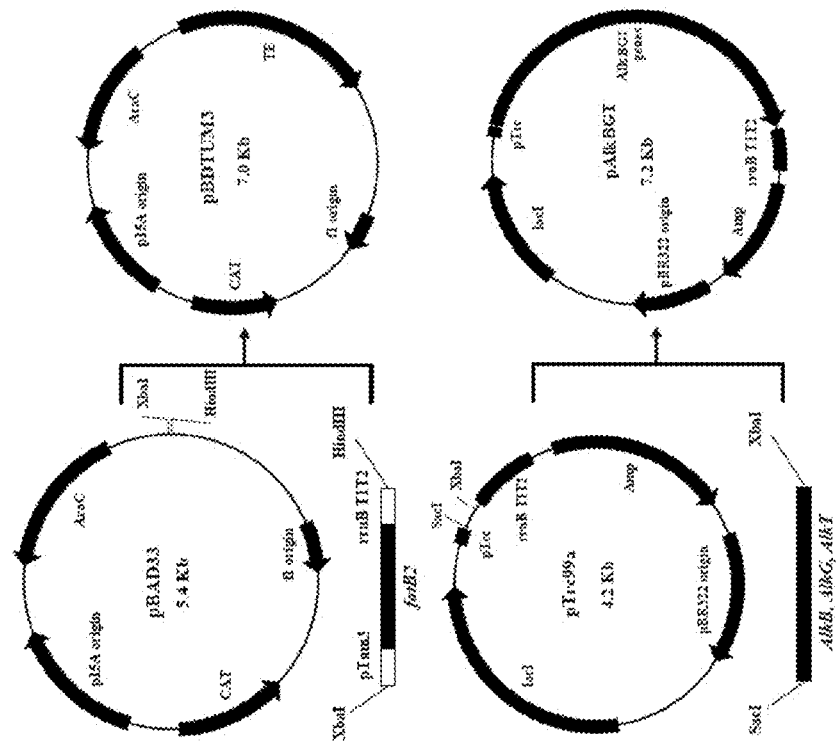

FIG. 2: Schematic diagram showing the construction of pBDTUM3 and pAlkBGT. Abbreviations: *fatB2* gene from *Cuphea hookeriana*; *AlkBGT* genes from *Pseudomonas putida* P1; pTum3, mutational trc promoter; rrnB T1T2, rrnB terminator; p15A origin, origin of replication of plasmid p15A; CAT, chloromycetin resistance gene; pTrc, trc promoter; lacI: *lac* operon repressor; Amp, ampicillin resistant gene; pBR322 origin, origin of replication of plasmid pBR322; restriction enzyme sites: XbaI, HindIII, SacI.

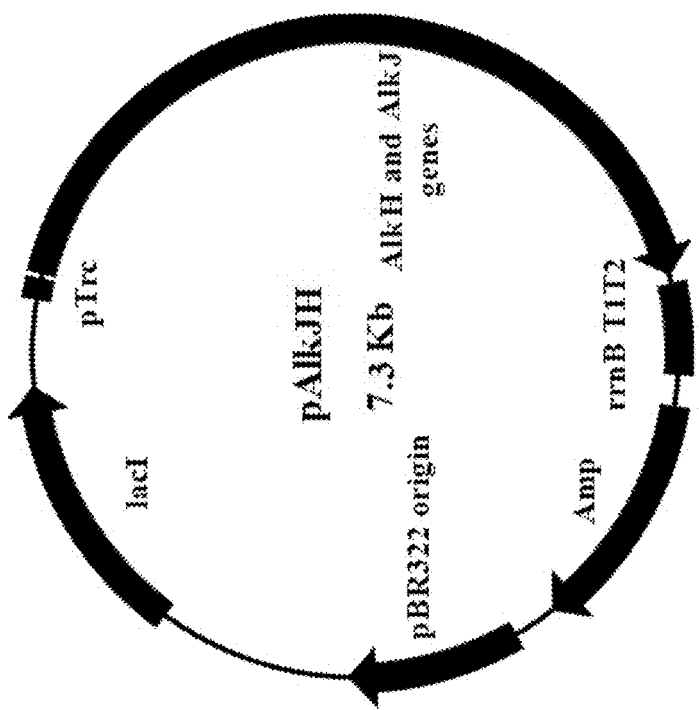
FIG. 3. Schematic diagram of the pAlkJH. Abbreviations: AlkHJ genes from *Pseudomonas putida* P1; pTrc, trc promoter; lacI: *lac* operon repressor; Amp, ampicillin resistant gene; pBR322 origin, origin of replication of plasmid pBR322; rrnBT1,2, transcriptional terminator of *rrnB*.

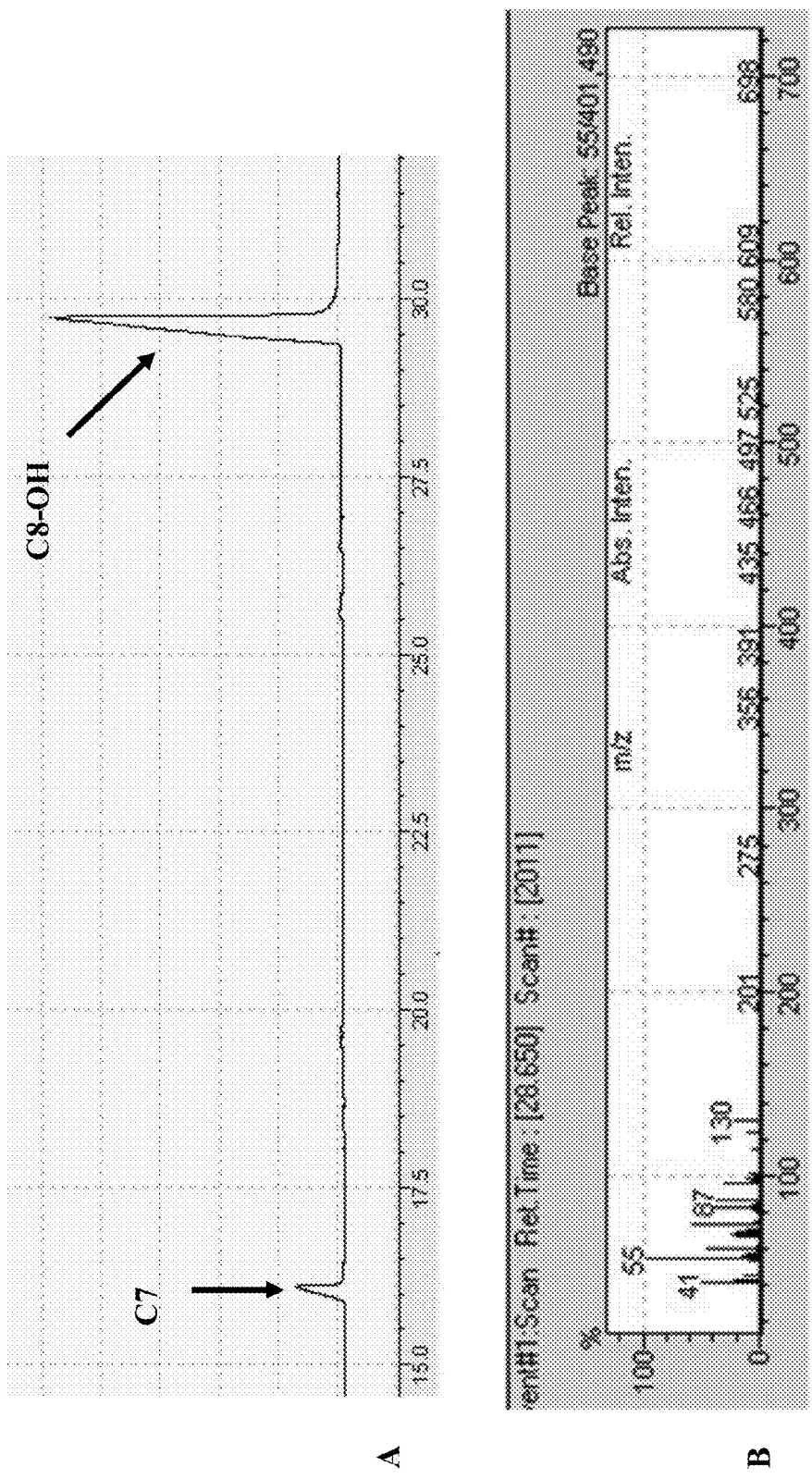
FIG. 4. Profile of heptanoic acid (C7) and hydroxyoctanoic acid (C8-OH) standards using GC-MS. A) GC chromatogram of hydroxyoctanoic acid (C8-OH); B) MS1 of hydroxyoctanoic acid

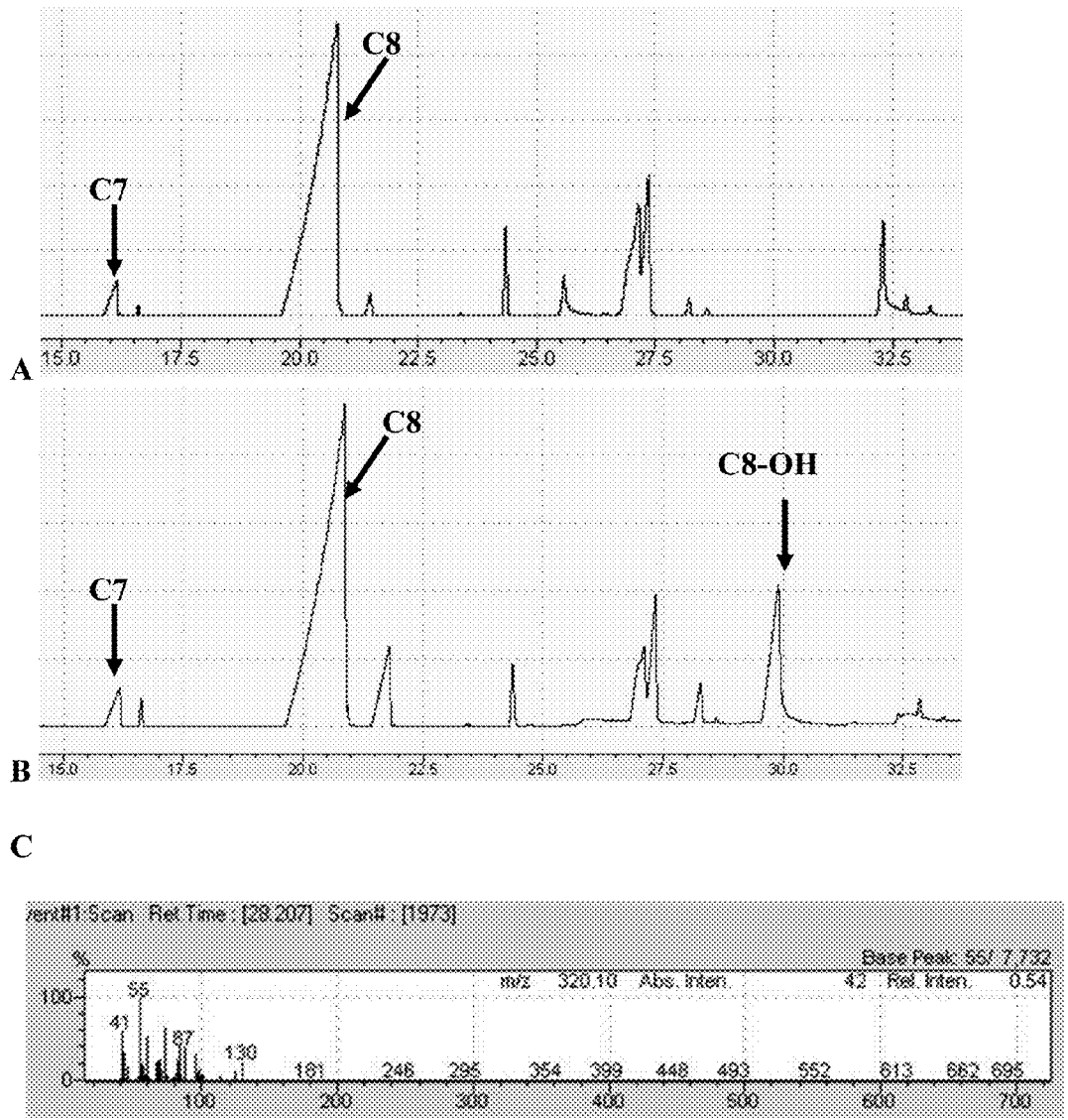
FIG. 5. Identification of octanoic acid (C8) and hydroxyoctanoic acid (C8-OH) using GC-MS from samples. Heptanoic acid (C7) was used as internal standard. A) GC chromatogram of sample K272 (pALK + pBDTUM3) with no IPTG; B) GC chromatogram of sample K272 (pALK + pBDTUM3) with 100 mM IPTG; C) MS1 of hydroxyoctanoic acid from sample K272 (pALK + pBDTUM3) with 100 mM IPTG.

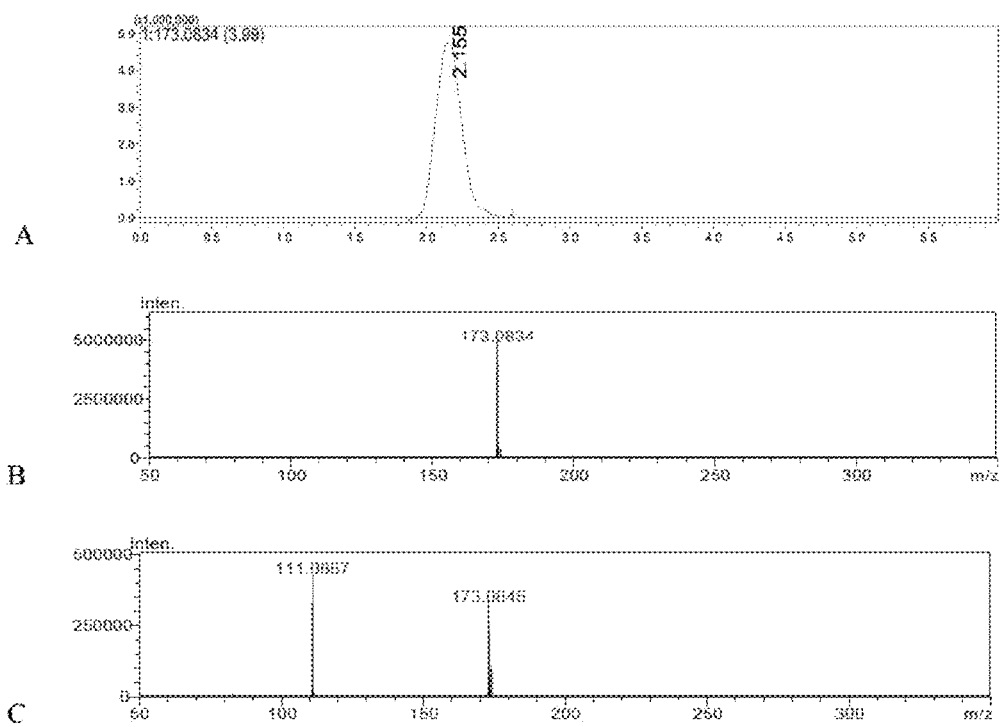
FIG. 6 Profile of commercial suberic acid (C8) using LC-MS. A) Extracted ion chromatogram (EIC) of suberic acid (m/z =173.0); B) MS1 of suberic acid (m/z = 173.0); (C) MS/MS of suberic acid (m/z 173.0 -> m/z 111.0).

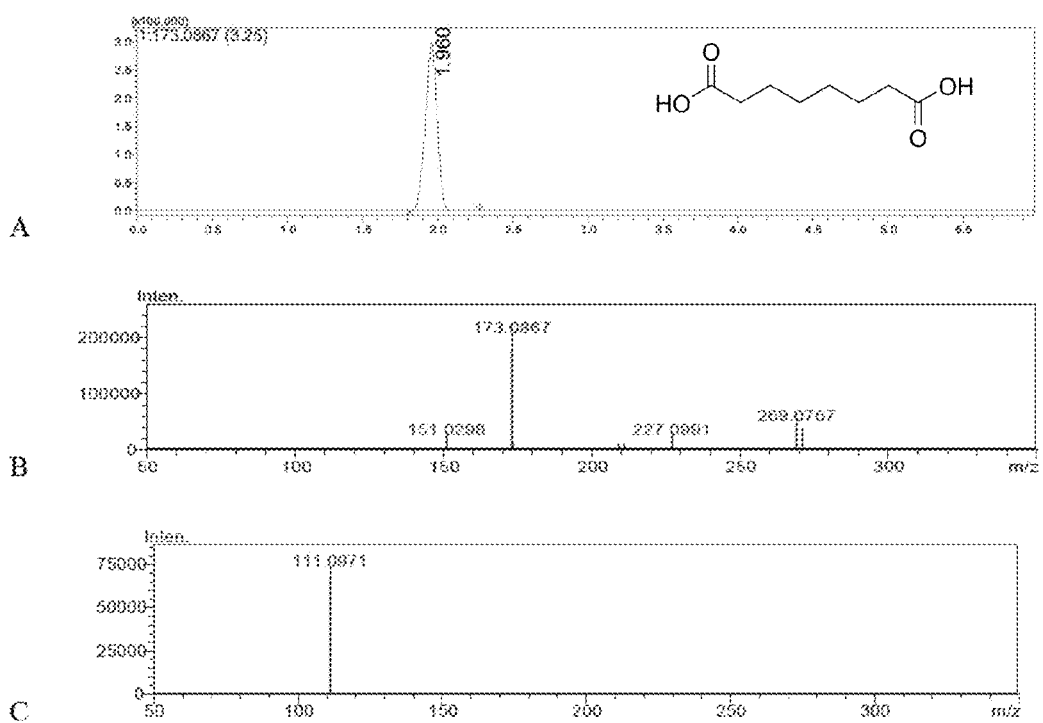
FIG. 7 Identification of suberic acid (C8) using LC-MS from samples. A) Extracted ion chromatogram (EIC) of suberic acid from sample, a mixed culture of MG1655 (pAlkBGT) and MG1655 (pAlkJH) at 48 h; B) MS1 of suberic acid (m/z = 173.0); (C) MS/MS of suberic acid (m/z 173.0 -> m/z 111.0).

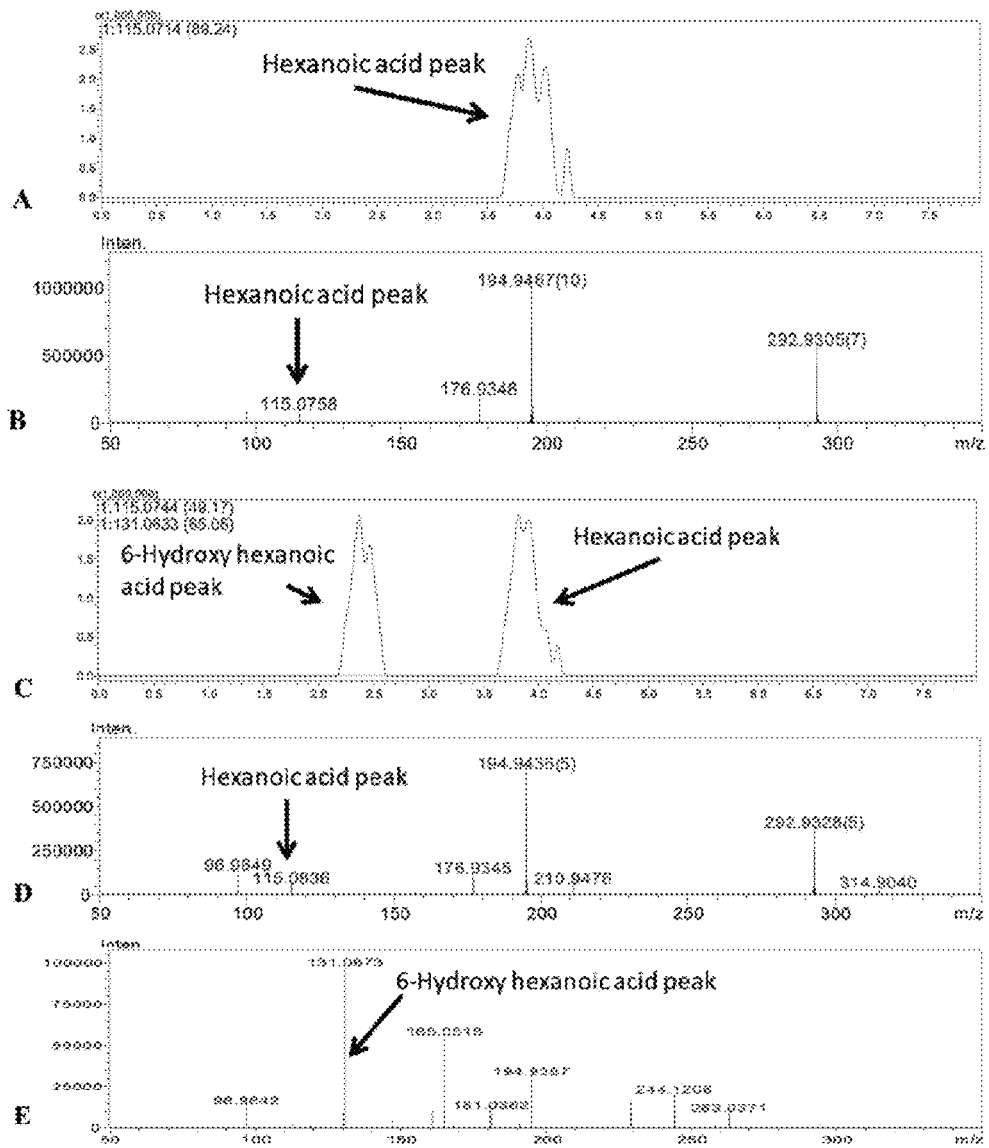
FIG. 8 Profile of hexanoic (C6) and 6-Hydroxyhexanoic acid (C6-OH) using LC-MS. A) Extracted ion chromatogram of hexanoic acid in the sample at 0h ; B) MS1 of hexanoic acid (m/z = 115) in the sample at 0h; C) Extracted ion chromatogram of 6-Hydroxyhexanoic acid and hexanoic acid at 24h; D) MS1 of hexanoic acid (m/z = 115); E) MS1 of 6-hydroxyhexanoic acid (m/z 131).

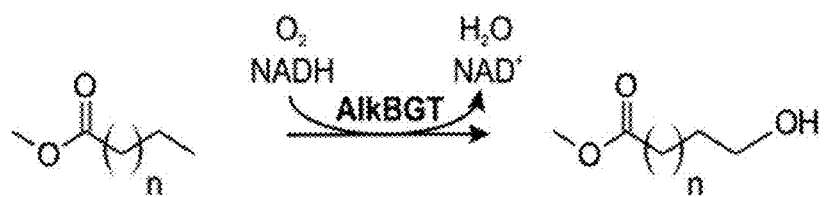
FIG. 9 AlkBGT reactions
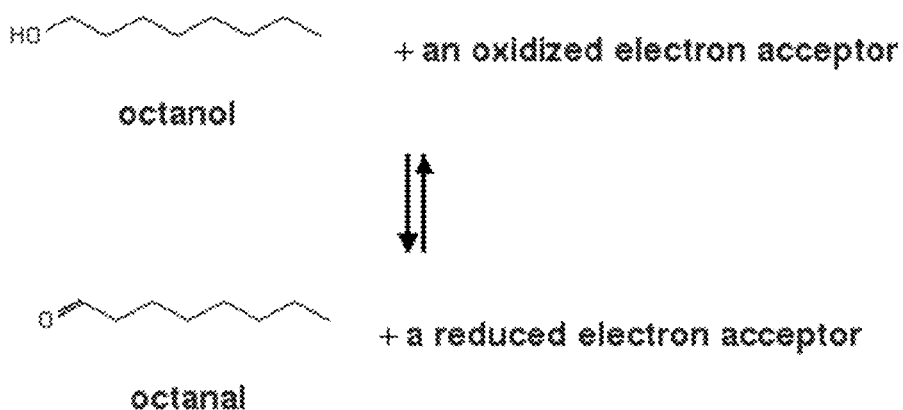
FIG. 10 AlkJ reaction [EC Number: 1.1.99]
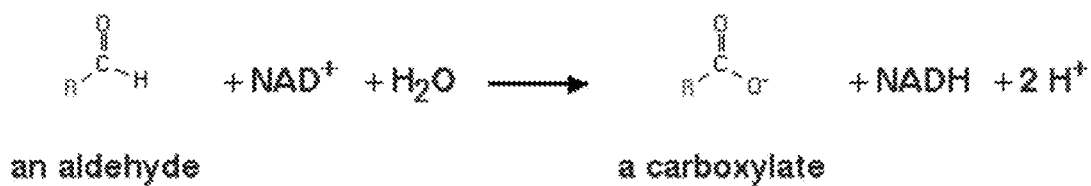
FIG. 11 AlkH reaction [EC Number: 1.2.1.3]

HYDROXY- AND DICARBOXYLIC-FAT SYNTHSIS BY MICROBES

PRIOR RELATED APPLICATIONS

This application claims priority to U.S. Ser. No. 61/939,567, filed Feb. 13, 2014, incorporated by reference herein in its entirety for all purposes.

FEDERALLY SPONSORED RESEARCH STATEMENT

This invention was made with government support under EEC-0813570 awarded by the NSF. The government has certain rights in the invention.

FIELD OF THE DISCLOSURE

The disclosure generally relates to microbial production of fatty acids.

BACKGROUND OF THE DISCLOSURE

Increasing energy costs and environmental concerns have emphasized the need to produce sustainable renewable fuels and chemicals. Fatty acids are composed of long alkyl chains and represent nature's "petroleum," being a primary metabolite used by cells for both chemical and energy storage functions. These energy-rich molecules are today isolated from plant and animal oils for a diverse set of products ranging from fuels to oleochemicals.

Whereas microbial fermentation processes for producing ethanol and related alcohol biofuels are well established, biodiesel (methylesters of fatty acids) is the major long chain product produced biologically, and it is almost exclusively derived from plant oils today. However, slow cycle times for engineering oil seed metabolism and the excessive accumulation of glycerol as a byproduct are two major drawbacks of deriving biodiesel from plants.

Although most bacteria do produce fatty acids as cell envelope precursors, the biosynthesis of fatty acids is tightly regulated at multiple levels and large quantities are not made. Thus, the production of fatty acids from bacteria has not yet reached the point where it is cost effective.

Our laboratory has already made considerable progress in engineering bacteria to produce more free fatty acids than are normally found in native bacteria. WO2011116279 for example, describes a recombinant bacterium comprising at least one overexpressed acyl-ACP thioesterase gene, and wherein at least one gene from the tricarboxylic acid cycle or glycolysis or both is inactivated to drive carbon in the direction of fat production. For example, an ACP thioesterase was combined with deletions in native fadD, and sucC. These bacteria have significantly increased overall fat levels.

WO2013096665 describes the next step in our work, which was to engineer a microorganism for producing enhanced amounts of long chain fatty acids, having an overexpressed acyl ACP thioesterase, and at least one mutated gene selected from the group consisting of fabR, fabZ, fadR, fabH and combinations thereof, and optionally including a inactivated sucC gene. Various bacteria in this category produce more long chain fats.

The next step was to enable the production of odd chain length fatty acids. Odd chain fatty acids can be made as described in US20140193867. In that application, the starting material was manipulated to be a C3 molecule, propionyl-CoA, by overexpressing a propionyl-CoA synthase gene. We also replaced the native β-ketoacyl-acyl carrier protein synthase III gene with one having a greater substrate preference for propionyl-coA than acetyl-coA. With these three modifications, greater odd chain fats were produced that was heretofore possible. In fact, >80% of the fats produced by such strains were of odd chain lengths.

The above genetic manipulations provided significant improvements in fat levels, and the excretion of visible amounts of fats also provided an easy method of collecting fats, while keeping the culture active and undisturbed, churning out more fats. Further, the addition of $Mg^{+2}$ to the culture allowed improved production as well.

Another improvement would be able to make hydroxyl- or dicarboxylated fatty acids. Hydroxy fatty acids widely used for making polymers are also valuable in chemical, cosmetic and food industries as starting materials for synthesis of lubricants, adhesives, and cosmetic ingredients. Similarly, dicarboxylic fatty acids have many industrial applications such as synthesis of copolymers like polyamides and polyesters, coatings, adhesives, greases, polyesters, dyestuffs, detergents, flame retardants, cosmetic ingredients, and fragrances. For example, adipic acid (n=6) is among the top 50 bulk manufactured chemicals in US primarily used for manufacturing nylon. Sebacic acid (n=8) and its derivatives have many applications used in manufacturing plasticizers, lubricants, and cosmetics. Dodecanedioic acid (n=12) is used in the production of nylon (nylon-6,12) and polyamides.

WO2013024114 describes the microbial preparation of co-functional carboxylic acids and carboxylic acid-functionalized co-esters. However, this method is not dependent on fatty acids as starting materials. Further, only a single experiment was performed, and the yields were quite poor.

This disclosure addresses some of those improvements.

SUMMARY OF THE DISCLOSURE

Hydroxy fatty acids and dicarboxylic fatty acids are typically produced by either a chemical process or by microbial transformation of aliphatic hydrocarbons and fatty acids. However, the existing genetically engineered *E. coli* strains provide an alternative method for production of hydroxy fatty acids and dicarboxylic fatty acids using microbial fermentation. If an alkane degradation pathway is added to a bacteria that already overexpresses an acyl ACP thioesterase, then hydroxy fatty acids and/or dicarboxylic fatty acids can be made.

The engineered microbes described herein can include other beneficial mutations.

For example, reduction or complete inactivation of one or more proteins in the TCA cycle or glycolysis, or both, as described in the inventors prior publications and applications for patent.

The TCA enzymes that can be reduced or inactivated include aconitase, isocitrate dehydrogenase, a-ketoglutarate dehydrogenase, succinyl-coA synthetase, succinic dehydrogenase, fumarase, malate dehydrogenase, and citrate synthase. In preferred embodiments the microorganism comprises inactivated succinyl-coA synthetase. In other embodiments, the organism is *E. coli* and the mutated TCA gene is the sucC gene, which encodes the succinyl-CoA synthetase beta subunit.

Glycolytic enzymes include hexokinase (aka glucokinase), phosphoglucose isomerase, phosphofructokinase, aldolase, triose phosphate isomerase, glyceraldehyde-3-phosphate dehydrogenase, phophoglycerate kinase, phophoglycerate mutate, enolase, pyruvate kinase, and the transport enzymes for glucose uptake, such as glucose phophotransferase (aka glucose permease).

Glucokinase and glucose phophotransferase are particularly preferred. In other embodiments, the organism is *E. coli* and the mutated glycolytic gene is pstG or glk.

Other mutations that can be combined with the bacteria herein include of i) overexpressed coenzyme A-acyl carrier protein transacylase, ii) overexpressed transhydrogenase, iii) moderately overexpressed acetyl-CoA carboxylase, and iv) reduced activity of endogenous fatty acyl-CoA synthetase.

The microbe can further comprise one or more of ΔsucC, ΔptsG, Δglk, ΔfabR, ΔackA, Δpta, ΔackA-pta, ΔpoxB, overexpression of genes involved in the fatty acid synthesis pathway (3-oxoacyl-[acyl-carrier-protein] reductase, hydroxyacyl-[ACP] dehydratase, enoyl-[ACP] reductase), overexpression of transhydrogenase (UdhA$^+$ and/or PntAB$^+$) and/or NAD kinase$^+$.

We sometimes use a fadD mutant strain as a base strain because it is often used in the literature and easily available. However, the fadD mutant is optional to the invention. In fact, we have previously shown that the strain ML103 (a fadD knockout mutant strain) and its parent strain MG1655 (lacking the fadD knockout) both accumulated similar quantities of free fatty acid when both with overexpressed acyl-ACP thioesterase (data not shown).

The advantages of using engineered microbes that overexpress both thioesterase and an alkane hydroxylase system simultaneously are as follows:

1) Ability to produce hydroxy fatty acids and dicarboxylic fatty acids of different chain length using different strain designs customized to produce specific chain length free fatty acids.

2) Extension of fatty acid synthesis pathway to produce new fatty acid derivatives that do not accumulate in wild type microorganism.

3) Ability to produce high value-added products using a non-destructive and environmentally safe method.

4) Utilization of inexpensive raw renewable feedstock as fermentation material.

5) A "green" renewable source of chemicals is provided.

The following gene sequences are exemplified herein, but many homologous sequences producing proteins of the same function can be used interchangeably herewith:

| Strain | Gene | GenBank Accession or Gene ID | Protein_ID |
|---|---|---|---|
| *Cuphea hookeriana* | fatB2 | U39834.1 | AAC49269 |
| *Pseudomonas putida* P1 | alkB | AJ233397 | CAB51047.1 |
| *Pseudomonas putida* P1 | alkG | AJ233397 | CAB51049.1 |
| *Pseudomonas putida* P1 | alkT | AJ233397 | CAB69078.1 |
| *Pseudomonas putida* P1 | alkJ | AJ233397 | CAB51051.1 |
| *Pseudomonas putida* P1 | alkH | AJ233397 | CAB51050.1 |

The disclosure includes one or more of the following embodiments, in any combinations thereof:

An engineered microbe comprising an overexpressed acyl-ACP thioesterase (TE) and an overexpressed alkane hydroxylase pathway that can oxidize free fatty acid to hydroxy fatty acids and dicarboxylic fatty acids. Preferably, the TE is from *Cuphea*, which is a much more robust and active enzyme than many others.

An engineered microbe comprising an overexpressed acyl-ACP thioesterase (TE) and an overexpressed alkane hydroxylase pathway that can oxidize free fatty acid to hydroxy fatty acids or dicarboxylic fatty acids, wherein said microbe makes at least 0.1 g/L (or >0.2 g/L or >0.4 g/L or >0.45 g/L) hydroxy fatty acids or dicarboxylic fatty acids.

An engineered microbe, said microbe being *E. coli* comprising TE$^+$; AlkB$^+$, AlkG$^+$ and AlkT$^+$, wherein said microbe makes at least 0.1 g/L (or >0.2 g/L or >0.4 g/L or >0.45 g/L) hydroxy fatty acids.

An engineered microbe, said microbe being *E. coli* comprising TE$^+$; AlkJ$^+$ and AlkH$^+$, wherein said microbe makes at least 0.1 g/L dicarboxylic fatty acids.

An engineered *E. coli* comprising TE$^+$, AlkB$^+$, AlkG$^+$ and AlkT$^+$

An engineered *E. coli* comprising TE$^+$, AlkJ$^+$ and AlkH$^+$.

A method of making hydroxyl- or dicarboxylated fatty acids, comprising growing the microbes herein described in a nutrient broth, allowing said bacteria to make hydroxyl- or dicarboxylated fatty acids, and isolating said hydroxyl- or dicarboxylated fatty acids.

A method of making hydroxyl- or dicarboxylated fatty acids, comprising growing the microbe of any claim herein in a nutrient broth, allowing said microbe to make hydroxyl- or dicarboxylated fatty acids, and isolating said hydroxyl- or dicarboxylated fatty acids.

A method of making hydroxyl- or dicarboxylated fatty acids, comprising:

growing a first microbe comprising TE$^+$ in a nutrient broth;

allowing said first microbe to make and secrete fatty acids;

growing a second microbe comprising an overexpressed alkane hydroxylase pathway that can oxidize free fatty acid to hydroxy fatty acids or dicarboxylic fatty acids to uptake said secreted fatty acids and convert same to hydroxyl- or dicarboxylated fatty acids; and isolating said hydroxyl- or dicarboxylated fatty acids.

Preferred growth conditions for these bacteria include addition of the requisite selectable inducing agent for inducible plasmids, and the requisite antibiotic if vector maintenance is an issue. Otherwise, growth conditions are suitable for the host cell and expression vectors used.

A method wherein said first microbe and said second microbe are co-cultured together, or wherein said first microbe and said second microbe are cultured separately, and further comprising collecting said secreted fatty acids and adding same to said second microbe. Preferably, these separate cultures can be sequential batch cultures. Alternatively, separate continuous cultures can be made, wherein culture medium enriched for fatty acids is passed from the first culture to the second culture for uptake and use. As yet another alternative, the second culture can simply be provided with starting fats, and the first culture can either be omitted or used at a separate time or in a separate location.

Metabolically engineered *E. coli* strains that can produce hydroxy fatty acid of different chain lengths from renewable feed stock.

Metabolically engineered *E. coli* strains can produce dicarboxylic fatty acid of different chain lengths from renewable feed stock.

The alkane hydroxylase system from bacteria can oxidize free fatty acid to hydroxy fatty acid and dicarboxylic fatty acid.

The alkane hydroxylase system having two modules: one can oxidize alkane or free fatty acid to hydroxy fatty acid, another one can oxidize hydroxyalkane or hydroxy fatty acid dicarboxylic fatty acid.

These two modules can be used together in one strain to produce dicarboxylic fatty acid from free fatty acid.

These two modules can be used in the same strain to produce free fatty acid and synthesize dicarboxylic fatty acid of different chain length from renewable feedstocks.

These two modules can be used in different strains. The mix culture of these strains can also produce hydroxy fatty acid or dicarboxylic fatty acid of different chain length from free fatty acid or directly from feed stock as carbon source.

The TE$^+$ can be a third module, and the three modules can be used in the same bacteria or not, as described herein. In yet other embodiments, one or more of the modules is incorporated into the genome of the bacteria so that selective pressure is not longer needed for vector maintenance. In yet other embodiments, the modules are optimized by selecting strong promoters and using codon optimized genes for the chosen host species. In still other embodiments, the bacteria of the invention are combined with further mutations, as herein described, to drive carbon use towards free fatty acid, and then hydroxy fatty acid or dicarboxylic fatty acid as desired.

Once an exemplary protein is obtained, many additional examples proteins of similar activity can be identified by BLAST search. Further, every protein record is linked to a gene record, making it easy to design overexpression vectors. Many of the needed enzymes are already available in expression vectors, and can often be obtained from cell depositories or from the researchers who cloned them. But, if necessary, new clones can be prepared based on available sequence information using RT-PCR techniques. Thus, it should be easily possible to obtain all of the needed enzymes for overexpression.

Understanding the inherent degeneracy of the genetic code allows one of ordinary skill in the art to design multiple nucleotide sequences that encode the same amino acid sequence. NCBI™ provides codon usage databases for optimizing DNA sequences for protein expression in various species. Using such databases, a gene or cDNA may be "optimized" for expression in *E. coli*, yeast, algal or other species using the codon bias for the species in which the gene will be expressed. Indeed, many programs are freely available for this purpose.

Initial cloning experiments have proceeded in *E. coli* for convenience since most of the required genes were already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella,* and *Streptococcus,* or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at http://en.wikipedia.org/wiki/List_of_sequenced_bacterial_genomes.

Additionally, yeast are a common species used for microbial manufacturing, and many species can be successfully transformed. In fact, rat acyl ACP thioesterase has already been successfully expressed in yeast *Saccharomyces*. Other species include but are not limited to *Candida, Aspergillus, Arxula adeninivorans, Candida boidinii, Hansenula polymorphs (Pichia angusta), Kluyveromyces lactis, Pichia pastoris, Saccharomyces cerevisiae* and *Yarrowia lipolytica*, to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira,* and *Laminaria japonica,* and the like. Indeed, the microalga Pavlova lutheri is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., Addgene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome or via expression vectors, as desired.

Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ one or more expression plasmids hosting 3 or more ORFs for convenience, but it may be preferred to insert operons or individual genes into the genome for stability reasons.

Still further improvements in yield can be had be removing competing pathways, such as those pathways for making e.g., acetate, formate, ethanol, and lactate, and it is already well known in the art how to reduce or knockout these pathways. See e.g., the inventors prior patents.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova TA & Madden TL (1999) FEMS Microbiol. Lett. 174:247-250, and available through the NCBI website. The default parameters were used, except the filters were turned OFF.

"Operably associated" or "operably linked", as used herein, refer to functionally coupled nucleic acid or amino acid sequences.

"Recombinant" is relating to, derived from, or containing genetically engineered material. In other words, the genome was intentionally manipulated in some way.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like.

By "null" or "knockout" what is meant is that the mutation produces undetectable active protein. A gene can be completely (100%) reduced by knockout or removal of part of all of the gene sequence. Use of a frame shift mutation, early stop codon, point mutations of critical residues, or deletions or insertions, and the like, can also completely inactivate (100%) gene product by completely preventing transcription and/or translation of active protein. All null mutants herein are signified by Δ.

"Overexpression" or "overexpressed" is defined herein to be at least 150% of protein activity as compared with an appropriate control species, or any expression in a species that lacks the activity altogether. Preferably, the activity is increased 100-500%. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

In certain species it is also possible to genetically engineer the endogenous protein to be overexpressed by changing the regulatory sequences or removing repressors. However, overexpressing the gene by inclusion on selectable plasmids that exist in hundreds of copies in the cell may be preferred due to its simplicity and ease of exerting externals controls, although permanent modifications to the genome may be preferred in the long term for stability reasons.

As used herein, the expressions "microorganism," "microbe," "bacteria", "strain" and the like may be used interchangeably and all such designations include progeny. It is also understood that all progeny may not be precisely identical in DNA content, due to deliberate or inadvertent mutations. Mutant progeny that have the same function or biological activity as recited in the claim are included. Where distinct designations are intended, it will be clear from the context.

Reference to proteins herein can be understood to include reference to the gene encoding such protein. Thus, a claimed "permease" protein can include the related gene encoding that permease. However, it is preferred herein to refer to the protein by standard name per ecoliwiki, e.g., Pgi is glucose-phosphate isomerase, since both enzymatic and gene names have varied widely in the prokaryotic arts. Reference to proteins herein can be understood to include reference to the gene encoding such protein.

Acyl-acyl carrier protein (ACP) thioesterase is an enzyme that terminates the intraplastidial fatty acid synthesis in plants by hydrolyzing the acyl-ACP intermediates and releasing free fatty acids to be incorporated into glycerolipids. These enzymes are classified in two families, FatA and FatB, which differ in amino acid sequence and substrate specificity. Generally speaking, the N terminal (aa 1-98) of any acyl-ACP thioesterases controls the substrate specificity of the enzyme, and it is known how to change substrate specificity by swapping amino terminal domains.

Many acyl-ACP thioesterase proteins are known and can be added to bacteria for use in the invention (e.g., CAA52070, YP 003274948, ACY23055, AAB71729, BAB33929, to provide the accession numbers for a few of the thousands of such proteins available), although we have used plasmids encoded plant genes herein. Such genes can be added by plasmid or other vector, or can be cloned directly into the genome.

Other acyl ACP thioesterases include *Umbellularia californica* (AAC49001), *Cinnamomum camphora* (Q39473), *Umbellularia californica* fatty acyl-ACP thioesterase (Q41635), *Myristica fragrans* (AAB71729), *Myristica fragrans* (AAB71730), *Elaeis guineensis* (ABD83939), *Elaeis guineensis* (AAD42220), *Populus tomentosa* (ABC47311), *Arabidopsis thaliana* (NP 172327), *Arabidopsis thaliana* (CAA85387), *Arabidopsis thaliana* (CAA85388), *Gossypium hirsutum* (Q9SQI3), *Cuphea lanceolata* (CAA54060), *Cuphea hookeriana* (AAC72882), *Cuphea calophylla* subsp. *mesostemon* (ABB71581), *Cuphea lanceolata* (CAC19933), *Elaeis guineensis* (AAL15645), *Cuphea hookeriana* (Q39513), *Gossypium hirsutum* (AAD01982), *Vitis vinifera* (CAN81819), *Garcinia mangostana* (AAB51525), *Brassica juncea* (ABI18986), *Madhuca longifolia* (AAX51637), *Brassica napus* (ABH11710), *Oryza sativa* (indica cultivar-group) (EAY86877), *Oryza sativa* (japonica cultivar-group) (NP-001068400), *Oryza sativa* (indica cultivar-group) (EAY99617), and *Cuphea hookeriana* (AAC49269).

In some embodiments, at least one acyl-ACP thioesterase gene is from a plant, for example overexpressed TE from *Ricinus communis* (XP_002515564.1), *Jatropha curcas* (ABU96744.1), *Diploknema butyracea* (AAX51636.1), *Cuphea palustris* (AAC49180.1), or *Gossypium hirsutum* (AAF02215.1 or AF076535.1), or an overexpressed hybrid TE comprising different thioesterase domains operably fused together (see WO2011116279, all sequences expressly incorporated by reference herein). Preferably, the hybrid thioesterase includes an amino terminal region (~aa 1-98 controls substrate specificity) of the acyl-ACP thioesterase from *Ricinus communis* or a 70, 80, 90 or 95% homolog thereto, or any TE with the desired substrate specificity, operably coupled to the remaining portion of the thioesterase from another species. In such manner, enzyme specificity can be tailored for the use in question.

A great number of TE proteins were characterized by Jing, and some of his results reproduced here:

| Kingdom | Subfamily | ACC No./ Name | Organism | Rationale for synthesis[a] | Total FA[b] (nmol/mL) |
|---|---|---|---|---|---|
| Planta | A | AAC49179[c, d] | *Cuphea palustris* | A (Bimodal specificity for C8 and C10 substrates) [1] | 708 ± 45 |
|  |  | AAB71731 | *Ulmus americana* | A (Broad specificity; highest activity on C10 and C16) [13] | 1098 ± 62 |
|  |  | AAG43857 | *Iris germanica* | B | 261 ± 20 |
|  |  | AAG43858 | *Iris germanica* | B | 14.8 ± 4.6 |
|  |  | EER87824 | *Sorghum bicolor* | B (Member of a Subfamily A Poeceae TE cluster) | 126 ± 13 |
|  |  | EER88593 | *Sorghum bicolor* | B (Member of a Subfamily A Poeceae TE cluster) | 90.7 ± 8.0 |
|  |  | CnFatB1 | *Cocos nucifera* | C | 130 ± 12 |
|  |  | CnFatB2 | *Cocos nucifera* | C | 572 ± 32 |
|  |  | CnFatB3 | *Cocos nucifera* | C | 200 ± 11 |
|  |  | CvFatB1 | *Cuphea viscosissima* | C | 79.2 ± 9.7 |
|  |  | CvFatB2 | *Cuphea viscosissima* | C | 249 ± 9 |

-continued

| Kingdom | Subfamily | ACC No./Name | Organism | Rationale for synthesis[a] | Total FA[b] (nmol/mL) |
|---|---|---|---|---|---|
| | | CvFatB3 | *Cuphea viscosissima* | C | 18.9 ± 2.1 |
| | | AAD42220 | *Elaeis guineensis* | C | 36.7 ± 3.8 |
| | B | EDQ65090 | *Physcomitrella patens* | B (Member of novel plant subfamily) | 380 ± 29 |
| | | EER96252 | *Sorghum bicolor* | B (Member of novel plant subfamily) | 175 ± 11 |
| | | EES11622 | *Sorghum bicolor* | B (Member of novel plant subfamily) | 9.43 ± 2.03 |
| | D | EEH52851 | *Micromonas pusilla* | B | 16.3 ± 1.6 |
| Bacteria | E | ACL08376 | *Desulfovibrio vulgaris* | D (Medium-chain linear, branched, and hydroxy fatty acids) [29] | 330 ± 9 |
| | F | CAH09236 | *Bacteroides fragilis* | D (Hydroxy fatty acids) [29] | 215 ± 6 |
| | | ABR43801 | *Parabacteroides distasonis* | D (Branched and branched hydroxy fatty acids) [30] | 70.3 ± 4.4 |
| | | AAO77182[e] | *Bacteroides thetaiotaomicron* | D (Anteiso-branched and hydroxy fatty acids) [29] | 60.4 ± 2.9 |
| | G | ABG82470 | *Clostridium perfringens* | D (Medium-chain fatty acids) [31] | 72.0 ± 9.5 |
| | H | EEG55387 | *Clostridium asparagiforme* | B | 25.9 ± 4.2 |
| | | EET61113 | *Bryantella formatexigens* | B | 381 ± 3 |
| | I | EDV77528 | *Geobacillus* sp. | D (Iso-branched fatty acids) [32] | 64.9 ± 12.0 |
| | J | BAH81730 | *Streptococcus dysgalactiae* | D (Medium-chain and cyclic propane ring fatty acids) [29] | 623 ± 14 |
| | | ABJ63754 | *Lactobacillus brevis* | D (Medium-chain and cyclic propane ring fatty acids) [33] | 710 ± 10 |
| | | CAD63310[e] | *Lactobacillus plantarum* | D (Medium-chain 3'-hydroxy fatty acids) [33, 34] | 436 ± 10 |
| | Non-grouped | EEI82564 | *Anaerococcus tetradius* | D (Organism produces butyric acid) [35] | 1381 ± 146 |
| | | CAE80300 | *Bdellovibrio bacteriovorus* | D (Straight-chain odd-numbered fatty acids) [29] | 333 ± 18 |
| | | ABN54268 | *Clostridium thermocellum* | D (Branched-chain fatty acids) [29] | 97.7 ± 3.2 |

[a]A: Functionally characterized TEs; B: TE does not group near characterized TEs and/or no organism lipid profile information is available; C: TEs cloned from organisms known to produce MCFAs; D: Organism's lipid profile used and predominant fatty acid constituents identified in the organism are listed in parentheses.
[b]The data are represented as mean ± standard error (n = 4).
[c]All but the three *C. nucifera* sequences were codon-optimized for expression in *E. coli*.
[d]Transit peptides were removed from all plant sequences.
[e]Acyl-ACP TEs with known crystal structures.
TEs were expressed in *E. coli* K27, and free fatty acids (FAs) that accumulated in the medium were analyzed by GC-MS.

Thus it can be seen that hundreds of such TE proteins have been used, and are readily available for overexpression uses in the claimed bacteria.

We exemplified the disclosure herein using the alkane degradation pathway of *Psuedomonas putida*, but the homologs from other species can be used. For example, the spectrum of alkanes utilized by *Alcanivorax dieselolei* (C5-C36) (Liu 2005) is substantially broader than those of most other previously described alkane degraders and therefore these proteins may be particularly useful. Other alkane degrading bacterial genera are *Thalassolitus* (Yakimov 2004), *Oleiphilus* (Golyshin 2002). *Bacillus. Geobacillus* (Merchant 2006), *Thennus* (Meintanis 2006), *Oleispira* (Yakimov 2003), *Acinetobacter* (Throne-Holst 2007), *Rhodococcus* (Whyte 2002) and US20130052700. Indeed, more than 5000 alkB genes are listed at http://fungene.eme.ms-u.edu/hmm_details.spr?hmm_id=322 and additional genes are listed at Brenda at http://www.brenda-enzymes.org/enzyme.php?eeno=1.14.15.3 (each incorporated by reference herein in its entirety for all purposes), and the remaining genes can also be found at various sites. A few exemplary proteins are listed below, but this list is by no means exhaustive.

| Strain name | Gene name | Accession Number |
|---|---|---|
| *Acinetobacter* sp. ADP1 | alkRM | AJ002316 |
| *Mycobacterium tuberculosis* H37Rv | alkB | RV3252C |
| *Pseudomonas aeruginosa* PAO1 | alkB1 | PA2574 |
| *Pseudomonas aeruginosa* PAO1 | alkB2 | PA1525 |
| *Pseudomonas putida* GPo1 | alkB | CAB54050 |
| *Pseudomonas putida* P1 | alkB | AJ233397 |
| *Rhodococcus opacus* B4 | alkB | BAH50504 |
| *Alcanivorax dieselolei* B-5T | partial alkB gene | AY683540 |
| *Alcanivorax jadensis* T9, | partial alkB gene | AY683536 |
| *Alcanivorax venustensis* ISO4T, | partial alkB gene | AY683535 |
| *Mycobacterium smegmatis* str. MC2 155 | alkB | AFP38269 |
| *Nocardia cyriacigeorgica* GUH-2 | alkB | CCF63494 |
| *Burkholderia cenocepacia* H111 | alkB | CCE49828 |
| *Burkholderia lata* | alkB | ABB07682 |
| *Mycobacterium avium* 104 | alkB | ABK67940 |
| *Mycobacterium tuberculosis* KT-0070 | alkB | KCG48464 |

Additional enzymes/gene sequences for use herein can be found e.g., by blasting the protein sequence against the non-redundant (NR) database in GenBank. For example, the first protein AlkB (CAB51047) was blasted and hundreds of hits returned, a few of which are reported here:

Homologs for AlkB (CAB51047_ = Alkane 1-monooxygenase aka Alkane hydroxylase, gene = alkB

*Pseudomonas pelagia* 99% WP_022963145.1
*Pseudomonas* sp. G5 93% WP_020798864.1
*Pseudomonas mendocina* ymp 92% YP_001185946.1
*Pseudomonas aeruginosa* 93% WP_019396671.1
*Bradyrhizobium* sp. DFCI-1 80% WP_021075777.1
*Marinobacter aquaeolei* VT8 76% YP_957898.1
*Marinobacter hydrocarbonoclasticus* 76% YP_005430734.1
*Marinobacter aquaeolei* VT8 76% YP_957728.1
*Marinobacter* sp. EVN1 75% WP_023008026.1
*Marinobacter* sp. EN3 74% WP_023011587.1
*Alcanivorax* sp. 97CO-5 78% EUC70824.1
*Alcanivorax borkumensis* SK2 78% YP_694427.1
*Oceanicaulis* sp. HTCC2633 79% WP_009802138.1
*Marinobacter* sp. C1S70 77% BAC98365.1
*Citreicella* sp. 357 78% WP_009506508.1
*Marinobacter* sp. ES-1 74% WP_022988819.1
Remaining homologs omitted By "long chain" acyl-ACP thioesterase, what is meant herein, is that the TE produces a preponderance of long chain (>C12) fatty acids. Preferably, such TE produces more than 50% of a fatty acid >C12.

By "short chain" acyl-ACP thioesterase, what is meant herein, is that the TE produces a preponderance of short chain (≤C12) fatty acids. Preferably, such TE produces more than 50% of a fatty acid ≤C12.

The following abbreviations may be used herein:

| | |
|---|---|
| ACC | Acetyl-CoA carboxylase |
| acc | Gene encoding Acetyl-CoA carboxylase |
| ACP or acyl-ACP | Acyl-acyl carrier protein |
| AlkB | alkane-1-monooxygenase, encoded by alkB, alkBGT together convert FA to hydroxy fatty acid |
| AlkG | Rubredoxin, encoded by alkG |
| AlkH | aldehyde dehydrogenase, encoded by alkH, converts aldehydes to carboxylic acids, thus if a free FA is the starting material, the alkBGTJK proteins will produce dicarboxylic acids |
| AlkJ | alcohol dehydrogenase, AlkJ is membrane-bound and converts aliphatic medium-chain-length alcohols into aldehydes, encoded by alkJ |
| AlkT | rubredoxin reductase, encoded by alkT |
| FA | Fatty acid |
| FFA | Free fatty acid |
| fabD | Gene encoding malonyl CoA-acyl carrier protein transacylase aka FabD |
| fadD | Gene encoding fatty acyl-CoA synthetase |
| FatB2 | A TE from *Cuphea hookeriana* (Cigar plant), also in *Cocos nucifera* (Coconut palm); *Umbellularia californica* (California bay laurel); *C. palustris*, canola, etc., encoded by fatB2 |
| FID | Flame ionization detector |
| fumAC | Gene encoding both fumarase A aka FumA, fumarase C aka FumC |
| gapA | Gene encoding a component of glyceraldehyde 3-phosphate dehydrogenase-A complex aka GapA |
| GC/MS | Gas chromatography mass spectroscopy |
| glk | Gene encoding glucokinase aka Glk |
| gltA | Gene encoding citrate synthase aka GltA |
| HPLC | High performance liquid chromatography |
| IPTG | Isopropyl (β-D-1-thiogalactopyranoside |
| LB | Luria-Bertoni |
| NADK | NAD Kinase |
| NADPH | Nicotinamide adenosine dinucleotide phosphate hydride |
| pfkA | Gene encoding 6-phosphofructokinase-1 |
| ptsG | Gene encoding glucose phosphotransferase enzyme IIBC aka glucose permease aka PtsG |
| pykF | Gene encoding a component of pyruvate kinase I aka PykF |
| sucC | Gene encoding succinyl-CoA synthetase beta subunit aka SucC |
| TE | Thioesterase |
| TE$_{Rc}$ | Thioesterase from *Ricinus communis* |
| TIC | Total ion chromatogram |
| Prot$^+$ | Overexpressed protein "Prot" |
| prot$^+$ | Overexpressed gene encoding Prot |
| Δprot | Null mutant producing no detectable Prot activity |
| TesA | Native thioesterase from *E. coli* |

The use of the word "a" or "an" when used in conjunction with the term "comprising" in the claims or the specification means one or more than one, unless the context dictates otherwise. The use of the term "or" in the claims is used to mean "and/or" unless explicitly indicated to refer to alternatives only or if the alternatives are mutually exclusive.

The term "about" means the stated value plus or minus the margin of error of measurement or plus or minus 10% if no method of measurement is indicated.

The terms "comprise", "include" (and their variants) are open-ended linking verbs and allow the addition of other elements when used in a claim. "Consisting of" when used to introduce a claim element is closed, and 'consisting essentially of' is intermediate, being open to elements that don't materially change the invention, but closed to those that do.

DESCRIPTION OF FIGURES

FIG. 1: Diagram showing the genetically engineered biosynthetic pathway of hydroxy fatty acid and dicarboxylic fatty acid. The bold arrows in the dotted box represent the newly introduced pathway of fatty acid derivatives.

FIG. 2: Schematic diagram showing the construction of pBDTUM3 and pAlkBGT. Abbreviations: fatB2 gene from *Cuphea hookeriana;* AlkBGT genes from *Pseudomonas putida* P1; pTum3, mutational trc promoter; rrnB T1T2, rrnB terminator; p15A origin, origin of replication of plasmid p15A; CAT, chloromycetin resistance gene; pTrc, trc promoter; lacI: lac operon repressor; Amp, ampicillin resistant gene; pBR322 origin, origin of replication of plasmid pBR322; restriction enzyme sites: XbaI, HindIII, SacI.

FIG. 3. Schematic diagram of the pAlkJH Abbreviations. AlkHJ genes from *Pseudomonas putida* P1; pTrc, trc promoter; lacI: lac operon repressor; Amp, ampicillin resistant gene; pBR322 origin, origin of replication of plasmid pBR322; rrnBT1,2, transcriptional terminator of rrnB.

FIG. 4. Profile of heptanoic acid (C7) and hydroxyoctanoic acid (C8-OH) standards using GC-MS. A) GC chromatogram of hydroxyoctanoic acid (C8-OH); B) MS1 of hydroxyoctanoic acid.

FIG. 5. Identification of octanoic acid (C8) and hydroxyoctanoic acid (C8-OH) using GC-MS from samples. Heptanoic acid (C7) was used as internal standard. A) GC chromatogram of sample K272 (pALK+pBDTUM3) with no IPTG; B) GC chromatogram of sample K272 (pALK+pBDTUM3) with 100 mM IPTG; C) MS1 of hydroxyoctanoic acid from sample K272 (pALK+pBDTUM3) with 100 mM IPTG.

FIG. 6 Profile of commercial suberic acid (C8) using LC-MS. A) Extracted ion chromatogram (EIC) of suberic acid (m/z=173.0); B) MS1 of suberic acid (m/z=173.0); (C) MS/MS of suberic acid (m/z 173.0->m/z 111.0).

FIG. 7 Identification of suberic acid (C8) using LC-MS from samples. A) Extracted ion chromatogram (EIC) of suberic acid from sample, a mixed culture of MG1655 (pAlkBGT) and MG1655 (pAlkJH) at 48 h; B) MS1 of suberic acid (m/z=173.0); (C) MS/MS of suberic acid (m/z 173.0->m/z 111.0).

FIG. 8 Profile of hexanoic (C6) and 6-Hydroxyhexanoic acid (C6-OH) using LC-MS. A) Extracted ion chromatogram of hexanoic acid in the sample at 0 h; B) MS1 of hexanoic acid (m/z=115) in the sample at Oh; C) Extracted ion chromatogram of 6-Hydroxyhexanoic acid and hexanoic acid at 24 h; D) MS1 of hexanoic acid (m/z=115); E) MS1 of 6-hydroxyhexanoic acid (m/z 131).

FIG. 9 AlkBGT reactions [EC 1.14.15.3 (AlkB); EC Number: 1.18.1.1 (AlkT)] AlkG has no EC number yet.

FIG. 10 AlkJ reaction [EC Number: 1.1.99].

FIG. 11 AlkH reaction [EC Number: 1.2.1.3].

DETAILED DESCRIPTION

The invention generally includes microbes engineering to have TE$^+$ as well as overexpressed alkane degradation proteins or genes. The invention also includes method of using said microbes, e.g., to make fatty acid derivatives.

We used the existing TE$^+$ strains or vectors from our prior work herein. However, there are hundreds of available TE genes and proteins, as well as hybrid TE genes and proteins that can be used instead.

The most extensively characterized alkane degradation pathway is that encoded on the OCT plasmid of *P. putida* GPo1, formerly identified as *Pseudomonas oleovorans* GPo1. The first enzyme of this pathway is an integral-membrane non-heme di-iron monooxygenase, named AlkB, that hydroxylates alkanes at the terminal position AlkB requires two soluble electron transfer proteins named rubredoxin (AlkG) and rubredoxin reductase (AlkT). There are now at least 60 alkB homologs known, and they show fairly high sequence diversity. AlkJ converts the alcohol to an aldehyde, and alkK converts the aldehyde to carboxyl, as shown in the reaction pathway below.

Further, we exemplified the system in *E. coli*, which is the workhorse of microbial engineering. However, this system can be engineered into any bacteria, including e.g., *Bacillus subtilis, Staphylococcus aureus, Streptomyces peucetius*, and the like. The cloning methods are the same, although species-specific promoters and codon optimization for a given species may be used to improve yields.

In addition, the invention can be combined with other mutations to drive fat production. For example, at least one gene from the tricarboxylic acid cycle or glycolysis or both is inactivated to drive carbon in the direction of fat production. For example, in prior work an ACP thioesterase was combined with deletions in native sucC. These bacteria significantly increased overall fat levels. Additionally, other genes can be added to further improve recoveries. For example, the co-expression of the alkL gene of P. putida encoding an outer membrane protein with so-far-unknown function increased the dodecanoic acid methyl ester oxygenation activity of recombinant *E. coli* 28-fold (Julsing 2012).

Plasmids

The construction of pBDTUM3 and pAlkBGT were shown in FIG. 1. The 1.6 Kb fatB2 of *Cuphea hookeriana* plus Tum3 promoter and rrnB terminator was amplified from previously constructed plasmid pKMCH. The PCR fragments were digested by restriction enzymes, XbaI and HindIII, and ligated to plasmid pBAD33, which was also digested with XbaI and HindIII. The newly constructed pBDTUM3 (7.0 Kb) expressed the heterologous mature acyl-ATP thioesterase (TE) of *C. hookeriana* (AAC72882).

The synthesized alk operon including AlkB, AlkG and AlkT genes from *Pseudomonas putida* P1 was digested with SacI and XbaI, and ligated to plasmid pTrc99a which was also digested with SacI and XbaI. The newly constructed pAlkBGT (7.2 Kb) co-expresses the heterologous alkane-1-monooxygenase (AlkB), rubredoxin (AlkG) and rubredoxin reductase (AlkT) of *P. putida* P1.

The heterologous alcohol dehydrogenase (AlkJ) and aldehyde dehydrogenase (AlkH) of *P. putida* P1 were synthesized and cloned into pTrc99a to form pAlkJH (7.3 Kb) (FIG. 3).

Cultures

The metabolically engineered strain K272, a ptsG mutant of *E. coli* strain K27, was used in the initial experiments because this strain was an efficient host for short chain free fatty acid production.

A single colony of strain K272 (pAlkBGT) was inoculated into 5 ml of Luria-Bertani (LB) and incubated in an orbital shaker operated at 250 rpm at 30° C. overnight. The preculture was inoculated into a flask containing 40 mL of the culture medium with 1% (v/v) inoculum. The culture medium contained: tryptone 10 g/L, yeast extract 5 g/L, NaCl 5 g/L, glucose 15 g/L, octanoic acid 10 mM, ampicillin 100 µg/L, IPTG 100 µM, pH 7.5. Shake flask experiment was performed at 30° C. with shaking at 250 rpm for 24 h. The samples were extracted by ethyl acetate, then dried under $N_2$ flow, and re-dissolved with 1.5 ml chloroform. The hydroxyoctanoic acid concentration was quantified by GC-FID system (Table 1).

TABLE 1

Concentration of hydroxyoctanoic acid production at 24 h

| Strain | Relevant genotype | Culture Condition | Concentration of hydroxyoctanoic acid (g/L) |
|---|---|---|---|
| ps_Alk+: overexpression of alkane-1-monooxygenase (AlkB), rubredoxin (AlkG) and rubredoxin reductase (AlkT) from *Pseudomonas putida* P1 in pTrc99a | | | |
| K272 (pAlkBGT) | ΔptsG, ps_Alk+ | LB, 15 g/L glucose, 10 mM octanoci acid, 100 µM IPTG | 0.45 |

These results showed that a bacteria containing AlkBGT+ could make hydroxyoctanoic acid. Thus, the AlkBGT+ was functional in the host species of *E. coli*.

The next step was to combine this culture with a TE+ culture for conversion of secreted fatty acids to hydroxyoctanoic acid. The following experiment demonstrates this approach.

Strain K272 (pAlkBGT) and strain K272 (pBDTUM3) were inoculated into 5 ml of Luria-Bertani (LB) respectively and incubated in an orbital shaker operated at 250 rpm at 30° C. overnight. The two precultures were simultaneously inoculated into a flask containing 40 mL of the culture medium with 1% (v/v) inoculum. The co-culture medium contained: tryptone 10 g/L, yeast extract 5 g/L, NaCl 5 g/L, glucose 15 g/L, ampicillin 100 µg/L, IPTG 100 µM, pH 7.5. Shake flask experiment was performed at 30° C. with shaking at 250 rpm for 24 h. The samples were extracted by ethyl acetate, then dried under $N_2$ flow and re-dissolved with 1.5 ml chloroform. The hydroxyoctanoic acid concentration was quantified by GC-FID system (Table 2).

TABLE 2

Concentration of hydroxyoctanoic acid production at 24 h

| Strain | Relevant genotype | Culture Condition | Concentration of Hydroxyoctanoic acid (g/L) |
|---|---|---|---|
| ps_Alk+: overexpression of alkane-1-monooxygenase (AlkB), rubredoxin (AlkG) and rubredoxin reductase (AlkT) from *Pseudomonas putida* P1 in pTrc99a ch_TE+: overexpression of acyl-ACP thioesterase from *Cuphea hookeriana* in pBAD33 | | | |
| K272 (pAlkBGT) K272 (pBDTUM3) | ΔptsG, ps_Alk+ ΔptsG, ch_TE+ | LB, 15 g/L glucose, 100 µM IPTG | 0.19 |

These results indicated that co-culturing the two strains allows the first strain to make and secrete free fatty acids, which the second strain uses to make hydroxyoctanoic acid. Note, there were no other hydroxyl fatty acid products, because the strain K272 (pBDTUM3) can only produce octanoic acid (C8 fatty acid).

In the next experiment, we combined the two plasmids constructs into a single microbe, and again measured hydroxyoctanoic acid production.

Strain K272 (pAlkBGT, pBDTUM3) was inoculated into 5 ml of Luria-Bertani (LB) and incubated in an orbital shaker operated at 250 rpm at 30° C. overnight. The pre-culture was inoculated into a flask containing 40 mL of the culture medium with 1% (v/v) inoculum. The culture medium contained: tryptone 10 g/L, yeast extract 5 g/L, NaCl 5 g/L, glucose 15 g/L, ampicillin 100 µg/L, IPTG 100 µM, pH 7.5. Shake flask experiment was performed at 30° C. with shaking at 250 rpm for 24 h. The samples were extracted by ethyl acetate, then dried under $N_2$ flow and re-dissolved with 1.5 ml chloroform. The hydroxyoctanoic acid in the sample was identified by GC-MS system (FIG. 5) compared to the standard (FIG. 4). The hydroxyoctanoic acid concentration was quantified by GC-FID system (Table 3).

TABLE 3

Concentration of hydroxyoctanoic acid production at 24 h

| Strain | Relevant genotype | Culture Condition | Concentration of Hydroxyoctanoic acid (g/L) |
|---|---|---|---|
| ps_Alk+: overexpression of alkane-1-monooxygenase (AlkB), rubredoxin (AlkG) and rubredoxin reductase (AlkT) from *Pseudomonas putida* P1 in pTrc99a | | | |
| ch_TE+: overexpression of acyl-ACP thioesterase from *Cuphea hookeriana* in pBAD33 | | | |
| K272 (pAlkBGT, pBDTUM3) | ΔptsG, ps_Alk+, ch_TE+ | LB, 15 g/L glucose, 100 µM IPTG | 0.24 |

Production levels were improved in the bacterium having both plasmids. The results may be further optimized by strain engineering and process optimization.

In the next experiment, we combined the plasmid encoding proteins that convert free fatty acid to hydroxyl fatty acids (AlkBGT) with the plasmid encoding proteins needed to convert the hydroxyl fatty acids to dicarboxylic acids (AlkJH). In the first test, we co-cultured separate strains, each carrying a plasmid. Additionally, we used a parent strain with a different background in order to show that the method is generally applicable, and not specific to the parent strains employed.

The *E. coli* strain MG1655 (Genotype: F⁻ lambda⁻ ilvG⁻ rfb-50 rph-1; Serotype: OR:H48:K-) was used as host strain for each of the vectors. Strain MG1655 (pAlkBGT) and strain MG1655 (pAlkJH) were inoculated into 5 ml of Luria-Bertani (LB) respectively and incubated in an orbital shaker operated at 250 rpm at 30° C. overnight. The two precultures were inoculated into a flask containing 50 mL of the LB medium with 1% (v/v) inoculum, respectively. 100 µM IPTG are added in both of the cultures. After 6 hours incubation, these cells of two cultures are collected by centrifugation and re-suspended together in culture medium for 24 h and 48 h incubation. The co-culture medium contains: tryptone 10 g/L, yeast extract 5 g/L, NaCl 5 g/L, octanoic acid 20 mM (for use as a starting material), ampicillin 100 µg/L, IPTG 100 µM, pH 7.5. Shake flask experiment is performed at 30° C. with shaking at 250 rpm. The suberic acid was identified by LC-MS system as shown in FIGS. 6 and 7.

These results show that the co-culture produced the final product, suberic acid. Therefore, the octanoic acid was converted to suberic acid using the two expression plasmids encoding the alkane degradation pathway.

In the second co-culture test, we use hexanoic acid as the substrate, thus demonstrating applicability to other products.

Strains MG1655(pAlkBGT) and MG1655(pAlkJH) were cultured in the flasks containing 50 mL of the LB medium with 1% (v/v) inoculum. IPTG and ampicillin were added in the cultures. After 8-12 hours incubation, these cells were collected by centrifugation, washed by 0.95% NaCl solution and re-suspended together in culture medium for 24 h incubation. The co-culture medium contained hexanoic acid 20 mmol/L (for use as a starting material), ampicillin 100 µg/L, IPTG 100 µmol/L, pH 7.5. Shake flask experiment is performed at 30° C. with shaking at 250 rpm. The 6-Hydroxyhexanoic acid was identified by LC-MS system as shown in FIG. 8.

No dicarboxylate was detected, possibly due lack of uptake of the 6-hydroxyhexanoic by the MG1655(pAlkJH). We expect that issue would be eliminated in a single strain having all needed enzymes, or in a strain engineered to include a suitable transporter for the hydroxyl carboxylic acid.

The work is still in progress to combine both AlkBGT and pAlkJH+with a TE+ in the same strain, as the combined strains are expected to be simpler to use than a co-culture technique, but the preliminary results indicate that success is likely. Further work will be needed to optimize the system, by e.g., combining the various genes into a single plasmid or even a single operon and host strain manipulation to channel the carbon flux to the final product.

Prophetic Experiment 1

In this prophetic experiment, we plan to convert hydroxyl fatty acid to dicarboxylic using dodecanoic acid as the substrate using a co-culture technique. Strain MG1655 (pAlkBGT) and strain MG1655 (pAlkJH) are inoculated into 5 ml of Luria-Bertani (LB) respectively and incubated in an orbital shaker operated at 250 rpm at 30° C. overnight. The two precultures are inoculated into a flask containing 50 mL of the LB medium with 1% (v/v) inoculum, respectively. 100 µM IPTG are added in both of the cultures. After 8-12 hours incubation, these cells of two cultures are collected by centrifugation and re-suspended together in culture medium for 24 h and 48 h incubation. The culture medium contains: tryptone 10 g/L, yeast extract 5 g/L, NaCl 5 g/L, dodecanoic acid 20 mM as a starting material, ampicillin 100 µg/L, IPTG 100 µM, pH 7.5. Shake flask experiment is performed at 30° C. with shaking at 250 rpm. The dodecanedioic acid can be identified by LC-MS system.

Prophetic Experiment 2

In this prophetic experiment, we plan to put all the needed genes onto one plasmid and then into a single strain, thus avoiding co-culture methods. The operon of alkJH from *P. putida* P1 plus Trc promoter and rrnB terminator is amplified from pAlkJH and cloned into pAlkGBT to form pAlkGBTHJ (9.3 K). The newly constructed pAlkGBTHJ co-expresses the heterologous alkane-1-monooxygenase (AlkB), rubredoxin (AlkG) and rubredoxin reductase (AlkT), alcohol dehydrogenase (AlkJ) and aldehyde dehydrogenase (AlkH) of *P. putida* P1. This plasmid can be introduced into e.g., *E. coli*, *B. subtilus*, and the like.

Prophetic Experiment 3

In this prophetic experiment, we plan to convert hydroxyl fatty acid to dicarboxylic using 8-hydroxyoctanoic acid as the substrate. A single colony of strain K272 (pAlkJH) is inoculated into 5 ml of Luria-Bertani (LB) and incubates in an orbital shaker operated at 250 rpm at 30° C. overnight. The preculture is inoculated into a flask containing 40 mL of the culture medium with 1% (v/v) inoculum. The culture medium contains: tryptone 10 g/L, yeast extract 5 g/L, NaCl 5 g/L, glucose 15 g/L, 8-hydroxyoctanoic acid 10 mM, ampicillin 100 µg/L, IPTG 100 µM, pH 7.5. Shake flask experiment is performed at 30° C. with shaking at 250 rpm for 24 h. The suberic acid concentration can be identified and quantified by LC-MS system.

Prophetic Experiment 4

Strain K272 (pBDTUM3, pAlkBGT) and strain K272 (pAlkJH) are inoculated into 5 ml of Luria-Bertani (LB) respectively and incubated in an orbital shaker operated at 250 rpm at 30° C. overnight. The two precultures are inoculated into a flask containing 40 mL of the culture medium with 1% (v/v) inoculum, respectively. After 6-8 hours incubation, these two cultures are combined together and incubated for 24 h. The culture medium contains: tryptone 10 g/L, yeast extract 5 g/L, NaCl 5 g/L, glucose 15 g/L, ampicillin 100 µg/L, IPTG 100 µM, pH 7.5. Shake flask experiment is performed at 30° C. with shaking at 250 rpm. The suberic acid concentration can be identified and quantified by GC-MS system.

Prophetic Experiment 5

Strain K272 (pBDTUM3, pAlkBGTJH) is inoculated into 5 ml of Luria-Bertani (LB) and incubated in an orbital shaker operated at 250 rpm at 30° C. overnight. The preculture is inoculated into a flask containing 40 mL of the culture medium with 1% (v/v) inoculum. The culture medium contains: tryptone 10 g/L, yeast extract 5 g/L, NaCl 5 g/L, glucose 15 g/L, ampicillin 100 µg/L, IPTG 100 µM, pH 7.5. Shake flask experiment is performed at 30° C. with shaking at 250 rpm for 24 h. The suberic acid concentration can be identified and quantified by GC-MS system.

Prophetic Experiment 6

Although the *E. coli* has become a new focus for fatty acid production and some breakthroughs have been made recently, the traditional oleaginous microorganisms like microalgae, fungi and yeast are well studied and can also be used as host cells to create the microbes herein described. Thus, pBDTUM3 and/or pAlkBGTJH or equivalent vectors are introduced into other bacteria, microalgae, fungi or yeast to take advantage of the well developed cell transformation and culturing methods generally available for such hosts.

Alternatively, the host selected may already have an overexpressed TE. Several cells containing overexpressed TE proteins are already available, such as human and murine cells lines (Ishizuka 2004), simian cos cells (Soyombo 1997), yeast (Saerens 2006), *Arabidopsis thaliana* (Voelker 1992), *Pseudomonas aeruginosa* (Lee 2012), and various *Escherichae* strains. Thus, the addition of Al kBGTJH in a suitable expression vector to such cells will be fairly simple, and positive results are expected.

Yeast may be a preferred host as large scale fermentation techniques are well developed for yeast. Additionally, several commercially available yeast protein expression systems exist in organisms from the genera *Saccharomyces, Pichia, Kluyveromyces, Hansenula* and *Yarrowia*. A growing number of engineered yeast strains are becoming available for protein expression. Strains have been described that increase yield of secreted proteins, improve the performance of certain affinity tags, reduce proteolysis, define the composition of N-glycans, and permit non-native amino acids (e.g. selenomethionine) into proteins have been described. One yeast system that is commonly used for protein expression is *Kluyveromyces lactis*. *K. lactis* and *S. cerevisiae* are the only two yeasts classified by the NIH as Host-Vector I systems, an important biosafety designation, making these attractive hosts.

For transfer into yeast, the vector would be exchanged, by moving the AlkBGTJH coding region into a yeast expression vector, such as the pKLAC1 vector for *K. Lactis* or pD1201 for *S. cerevisiae*.

The following references are each incorporated herein in their entireties for all purposes.

US20140093921 Bacteria and method for synthesizing fatty acids
WO2013096665 Long chain organic acid bioproduction
US20140193867 Microbial odd chain fatty acids
US20140212935 Short chain fatty acids from bacteria
US20130052700 Biocatalytic oxidation process with alkl gene product
U.S. Pat. No. 7,901,924 Increased bacterial CoA and acetyl-CoA pools
U.S. Pat. No. 7,223,567 Mutant *E. coli* strain with increased succinic acid production
WO2013024114 Biotechnological synthesis process of omega-functionalized carbon acids and carbon acid esters from simple carbon sources Davis, M. S.; Cronan, J. E., Inhibition of *Escherichia coli* acetyl coenzyme A carboxylase by acyl-acyl carrier protein, Jr. J Bacteriol 183, 1499 (2001).

Golyshin P. N., et al., Oleiphilaceae fam. nov., to include *Oleiphilus messinensis* gen. nov., sp. nov., a novel marine-bacterium that obligately utilizes hydrocarbons. Int J Syst Evol Microbiol 52:901-911 (2002).

Heath, R. J. & Rock, C. O., Inhibition of beta-ketoacyl-acyl carrier protein synthase III (FabH) by acyl-acyl carrier protein in *Escherichia coli*, J Biol Chem 271, 10996 (1996a).

Heath, R. J. & Rock, C. O., Regulation of fatty acid elongation and initiation by acyl-acyl carrier protein in *Escherichia coli*, J Biol Chem 271, 1833 (1996b).

Ishizuka M., et al., Overexpression of human acyl-CoA thioesterase upregulates peroxisome biogenesis, Exp Cell Res. 2004 Jul. 1; 297(1):127-41.

Jing F., et al., Phylogenetic and experimental characterization of an acyl-ACP thioesterase family reveals significant diversity in enzymatic specificity and activity, BMC Biochemistry 12:44 (2011).

Julsing M. K., Outer membrane protein AlkL boosts biocatalytic oxyfunctionalization of hydrophobic substrates in *Escherichia coli*, Appl Environ Microbiol. 78(16):5724-33 (2012).

Lee S., et al., Heterologous co-expression of accA, fabD, and thioesterase genes for improving long-chain fatty acid production in *Pseudomonas aeruginosa* and *Escherichia coli*. Appl Biochem Biotechnol. 2012 May; 167(1):24-38.

Lee Sl, Jeon E, Jung Y, Lee J. Liu C. & Shao Z., *Alcanivorax dieselolei* sp. nov., a novel alkane-degrading bacterium isolated from sea water and deep-sea sediment. Int J Syst Evol Microbiol 55(3):1181-1186 (2005).

Marchant R., et al., The degradation of n-hexadecane in soil by Thermophilic geobacilli. FEMS Microbiol Ecol 56(1):44-54 (2006).

Meintanis C, et al., Biodegradation of crude oil by thermophilic bacteria isolated from a volcano island. Biodegradation 17:3-9 (2006).

Saerens S. M. G., et al., The *Saccharomyces cerevisiae* EHT1 and EEB1 genes encode novel enzymes with medium-chain fatty acid ethyl ester synthesis and hydrolysis capacity. J Biol Chem 281(7): 4446-4456 (2006).

Soyombo A., et al., Molecular Cloning and Expression of Palmitoyl-protein Thioesterase 2 (PPT2), a Homolog of Lysosomal Palmitoyl-protein Thioesterase with a Distinct Substrate Specificity, JBC 272(43): 27456-27463 (1997).

Throne-Holst, M., Identification of Novel Genes Involved in Long-Chain n-Alkane Degradation by *Acinetobacter* sp. Strain DSM 17874, Appl Environ Microbiol. 73(10): 3327-3332 (2007).

van Beilen J. B., DNA sequence determination and functional characterization of the OCT-plasmid-encoded a1kJKL genes of *Pseudomonas oleovorans*, Mol Microbiol. 6(21): 3121-36 (1992).

Voelker T. A. & Davies H. M., Alteration of the specificity and regulation of fatty acid synthesis of *Escherichia coli* by expression of a plant medium-chain acyl-acyl carrier protein thioesterase, J. Bacteriol. 176:7320-7327 (1994).

Whyte, L. G. Gene Cloning and Characterization of Multiple Alkane Hydroxylase Systems in *Rhodococcus Strains* Q15 and NRRL B-16531, Appl. Environ. Microbiol.68(12): 5933-5942 (2002).

Yakimov M. M., et al., *Oleispira antarctica* gen. nov., sp. nov., a novel hydrocarbonoclastic marine bacterium isolated from Antarctic coastal sea water. Int J Syst Evol Microbiol 53:779-785 (2003).

Yakimov M. M., et al., *Thalassolituus oleivorans* gen. nov., sp nov., a novel marine bacterium that obligately utilizes hydro-carbons. Int J Syst Evol Microbiol 54:141-148 (2004).

The invention claimed is:

1. An engineered microbe comprising an overexpressed acyl-ACP thioesterase (TE) and an overexpressed alkane hydroxylase pathway that can oxidize free fatty acid to hydroxy fatty acids or dicarboxylic fatty acids, wherein said microbe makes at least 0.1 g/L hydroxy fatty acids or dicarboxylic fatty acids.

2. The microbe of claim 1, further comprising a reduced activity of a protein in the TCA cycle.

3. The microbe of claim 1, further comprising a reduced activity of a protein in glycolysis.

4. The microbe of claim 1, said microbe comprising TE$^+$ and AlkBGT$^+$ wherein said microbe makes at least 0.1 g/L hydroxy fatty acids.

5. The microbe of claim 1, said microbe comprising TE$^+$ and AlkBGT$^+$ and AlkJH$^+$, wherein said microbe makes at least 0.1 g/L dicarboxylic fatty acids.

6. The microbe of claim 1, said microbe being *E. coli* comprising TE$^+$, AlkBGT$^+$, and AlkJH$^+$, wherein said microbe makes at least 0.1 g/L dicarboxylic fatty acids or hydroxy fatty acids or both.

7. The microbe of claim 1, further including one or more of ΔsucC, ΔptsG, Δglk, ΔfabR, ΔackA, Δpta, ΔackA-pta, ΔpoxB, 3-hydroxy-acyl-[acyl-carrier-protein] dehydratase$^+$, 3-oxoacyl-[acyl-carrier-protein] reductase$^+$, hydroxyacyl-[acyl-carrier-protein] dehydratase$^+$, enoyl-[acyl-carrier-protein] reductase$^+$, transhydrogenase$^+$, UdhA$^+$ PntAB$^+$, and/or NAD kinase$^+$.

8. The microbe of claim 1, wherein said TE is from *Cuphea*.

9. An engineered *E. coli* comprising i) TE$^+$, and ii) AlkBGT$^+$ and AlkJH$^+$, or AlkBGTJH$^+$.

10. The engineered *E. coli* of claim 9, further comprising one or more of ΔsucC, ΔptsG, Δglk, ΔfabR, ΔackA, Δpta, ΔackA-pta, ΔpoxB, 3-hydroxy-acyl-[acyl-carrier-protein] dehydratase 3-oxoacyl-[acyl-carrier-protein] reductase hydroxyacyl-[acyl-carrier-protein] dehydratase enoyl-[acyl-carrier-protein] reductase$^+$, transhydrogenase$^+$, UdhA$^+$ PntAB$^+$, and/or NAD kinase$^+$.

11. A method of making hydroxyl- or dicarboxylated fatty acids, comprising growing the microbe of claim 1 in a nutrient broth, allowing said microbe to make hydroxyl- or dicarboxylated fatty acids, and isolating said hydroxyl- or dicarboxylated fatty acids.

12. A method of making hydroxyl- or dicarboxylated fatty acids, comprising growing the microbe of claim 9 in a nutrient broth, allowing said microbe to make hydroxyl- or dicarboxylated fatty acids, and isolating said hydroxyl- or dicarboxylated fatty acids.

13. A method of making hydroxyl- or dicarboxylated fatty acids, comprising growing the microbe of claim 10 in a nutrient broth, allowing said microbe to make hydroxyl- or dicarboxylated fatty acids, and isolating said hydroxyl- or dicarboxylated fatty acids.

14. A method of making hydroxyl- or dicarboxylated fatty acids, comprising:
   a. growing a first microbe comprising TE in a nutrient broth;
   b. allowing said first microbe to make and secrete fatty acids;
   c. growing a second microbe comprising an overexpressed alkane hydroxylase pathway that can oxidize said fatty acid to hydroxy fatty acids or dicarboxylic fatty acids to uptake said secreted fatty acids and convert same to hydroxyl- or dicarboxylated fatty acids; and
   d. isolating said hydroxyl- or dicarboxylated fatty acids.

15. The method of claim 14, wherein said first microbe and said second microbe are co-cultured together.

16. The method of claim 14, wherein said first microbe and said second microbe are cultured separately, and further comprising collecting said secreted fatty acids and adding same to said second microbe.

* * * * *

UNITED STATES PATENT AND TRADEMARK OFFICE
CERTIFICATE OF CORRECTION

| | | |
|---|---|---|
| PATENT NO. | : 9,487,804 B2 | Page 1 of 1 |
| APPLICATION NO. | : 14/607624 | |
| DATED | : November 8, 2016 | |
| INVENTOR(S) | : Ka-Yiu San et al. | |

It is certified that error appears in the above-identified patent and that said Letters Patent is hereby corrected as shown below:

Claim 10 should read:

10. The engineered *E. coli* of claim 9, further comprising one or more of Δ*sucC*, Δ*ptsG*, Δ*glk*, Δ*fabR*, Δ*ackA*, Δ*pta*, Δ*ackA-pta*, Δ*poxB*, 3-hydroxy-acyl-[acyl-carrier-protein] dehydratase$^+$, 3-oxoacyl-[acyl-carrier-protein] reductase$^+$, hydroxyacyl-[acyl-carrier-protein] dehydratase$^+$, enoyl-[acyl-carrier-protein] reductase$^+$, transhydrogenase$^+$, UdhA$^+$ PntAB$^+$, and/or NAD kinase$^+$.

Signed and Sealed this
Fifteenth Day of August, 2017

Joseph Matal
*Performing the Functions and Duties of the
Under Secretary of Commerce for Intellectual Property and
Director of the United States Patent and Trademark Office*